United States Patent [19]

Dufetel et al.

[11] Patent Number: 5,610,302
[45] Date of Patent: Mar. 11, 1997

[54] COMPOSITION INTENDED FOR USE FOR RETARDING HAIR LOSS AND FOR INDUCING AND STIMULATING ITS GROWTH, CONTAINING 2-AMINOPYRIMIDINE 3-OXIDE DERIVATIVES, AND NEW COMPOUNDS DERIVED FROM 2-AMINOPYRIMIDINE 3-OXIDE

[75] Inventors: Didier Dufetel, Chelles; Francoise Estradier, Paris; Quintino Gaetani, Sevran; Michel Hocquaux, Paris, all of France

[73] Assignee: L'Oreal, Paris, France

[21] Appl. No.: 461,848

[22] Filed: Jun. 5, 1995

Related U.S. Application Data

[62] Division of Ser. No. 224,176, Apr. 7, 1994, which is a continuation of Ser. No. 573,578, Aug. 27, 1990, abandoned.

[30] Foreign Application Priority Data

Aug. 29, 1989 [FR] France .................. 89 11352

[51] Int. Cl.$^6$ .......................... C07D 239/22
[52] U.S. Cl. .......... 544/320; 544/321; 544/231; 544/253
[58] Field of Search ................... 544/320, 321, 544/231, 253

[56] References Cited

U.S. PATENT DOCUMENTS

| | | | |
|---|---|---|---|
| 3,464,987 | 9/1969 | Ursprung | 260/247.5 |
| 3,644,364 | 2/1972 | Anthony | 260/256.4 H |
| 4,013,778 | 3/1977 | Morrison | 424/251 |
| 4,287,338 | 9/1981 | McCall | 544/123 |
| 4,411,690 | 10/1983 | Tseng | 71/92 |
| 4,945,093 | 7/1990 | Naignan et al. | 514/235.8 |
| 4,985,425 | 1/1991 | Chiba et al. | 514/222.2 |

FOREIGN PATENT DOCUMENTS

| | | |
|---|---|---|
| 0042669 | 12/1981 | European Pat. Off. . |
| 0210227 | 7/1986 | European Pat. Off. . |
| 0303871 | 2/1989 | European Pat. Off. . |
| 1510247 | 12/1967 | France . |
| 3544267 | 6/1987 | Germany . |
| 2160710 | 6/1990 | Japan . |
| 2071092 | 9/1981 | United Kingdom . |

OTHER PUBLICATIONS

McCall, J. Med. Chem., 26, 1791–1793, 1983.
Jovanovic, Can. J. Chem., 62, 1176–1180, 1984.
Muller, Helv. Chim. Acta, 65, No. 143, Fasc. 5, 1454–1466, 1982.
The Merck Index, 11th ed., 976–977, No. 6122, 1989.
Chem. Abstr., vol. 68, p. 2116, No. 21947h, 1968.

Primary Examiner—John M. Ford
Attorney, Agent, or Firm—Jacobson, Price, Holman & Stern, PLLC

[57] ABSTRACT

Composition for retarding hair loss and for inducing and stimulating its growth, containing at least one compound of formula:

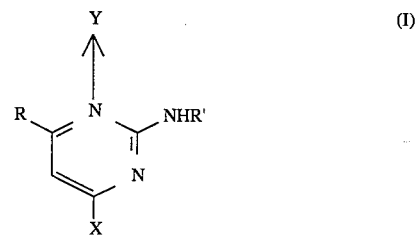

where R denotes H, alkyl or a ring of formula:

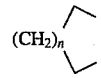

X denotes

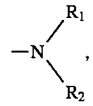

—OR$_3$, —SR$_4$ with:
the remaining variables defined below in the body of the specification.

2 Claims, No Drawings

COMPOSITION INTENDED FOR USE FOR RETARDING HAIR LOSS AND FOR INDUCING AND STIMULATING ITS GROWTH, CONTAINING 2-AMINOPYRIMIDINE 3-OXIDE DERIVATIVES, AND NEW COMPOUNDS DERIVED FROM 2-AMINOPYRIMIDINE 3-OXIDE

This is a division of application Ser. No. 08/224,176, filed Apr. 7, 1994, which is a continuation of application Ser. No. 07/573,578, filed Aug. 27, 1990, abandoned.

The invention relates to compositions intended for use, in particular in topical application, for retarding hair loss and for inducing and stimulating its growth, containing 2-aminopyrimidine 3-oxide derivatives, as well as to new 2-aminopyrimidine 3-oxide derivatives used in these compositions.

2,4-Diamino-6-piperidinopyrimidine 3-oxide or "minoxidil" is already known in the prior art for its properties as an antihypertensive agent, but also for its use in the treatment of hair loss, pelade, desquamating dermatitis and alopecia.

The Applicant has discovered new compositions for the treatment and prevention of hair loss, used, in particular, in topical application and especially efficacious in the treatment of diseases of the scalp as a result of a particular family of compounds derived from 2-aminopyrimidine 3-oxide.

The compounds selected by the Applicant, in addition to the fact that they are efficacious for hair regrowth and, in particular, for inducing and stimulating its growth and retarding its loss, exhibit substantially zero antihypertensive activity, or an activity lower than that of minoxidil.

These compounds possess solubilities in the media customarily used in cosmetics and in pharmacy which are markedly greater than those of minoxidil.

The subject of the invention is hence new compositions intended for the treatment and prevention of hair loss, containing particular compounds derived from 2-aminopyrimidine 3-oxide.

The subject of the invention is also new derivatives of 2-aminopyrimidine 3-oxide used in these compositions.

Another subject relates to the use of the compounds according to the invention for the preparation of a medicinal product intended for the therapeutic treatment of hair loss.

Other subjects of the invention will become apparent on reading the description and the examples which follow.

The compositions according to the invention are essentially characterized in that they contain, in a physiologically acceptable medium, at least one compound corresponding to the following formula:

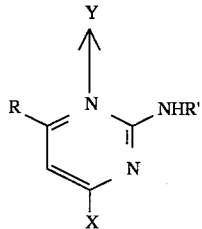

(I)

in which:

R denotes a hydrogen atom or a saturated linear $C_1$–$C_8$ alkyl radical or, with the pyrimidine ring, forms a carbon/hydrogen-containing ring of formula.

with n equal to 1, 2 or 3;

X denotes;
(i) a hydrogen atom;
(ii) a group

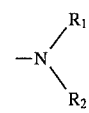

in which:

$R_1$ and $R_2$, which may be identical or different, denote a hydrogen atom, a saturated linear or branched $C_1$–$C_{12}$ alkyl group which can be substituted with a halogen atom or a trifluoromethyl radical, a linear $C_2$–$C_{12}$ alkenyl group, a $C_3$–$C_{10}$ cycloalkyl group, a $C_7$–$C_{12}$ aralkyl group or an aryl group corresponding to the formula:

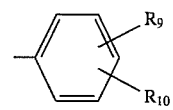

in which $R_9$ and $R_{10}$, which may be identical or different, denote hydrogen, $C_1$–$C_4$ alkyl, hydroxyl, $C_1$–$C_4$ alkoxy or halogen;

$R_1$ and $R_2$, with the nitrogen atom to which they are attached, can form a saturated or unsaturated heterocycle selected from the following groups: aziridino, azetidino, pyrrolidino, piperidino, hexamethylenimino, heptamethylenimino, octamethylenimino, tetrahydropyridino, dihydropyridino, pyrrole, pyrrazole, imidazole, triazole, 4-alkylpiperazino, morpholino, thiomorpholino;

(iii) a group —$OR_3$, in which $R_3$ denotes a saturated linear or branched $C_1$–$C_{12}$ alkyl radical which can be substituted with a halogen atom or a trifluoromethyl radical, a linear $C_2$–$C_{12}$ alkenyl radical, a $C_3$–$C_{10}$ cycloalkyl radical, a $C_7$–$C_{12}$ aralkyl radical or a phenyl radical optionally substituted with one or two groups which, independently of one another, denote a $C_1$–$C_6$ alkyl radical, a $C_1$–$C_6$ alkoxy radical, a halogen atom or a trifluoromethyl radical;

(iv) a group —$SR_4$, in which $R_4$ has the same meaning as $R_3$ defined above;

Y denotes an oxygen atom or an —$OSO_3^{\ominus}$ group; and

R' denotes a hydrogen atom or one of the following groups:

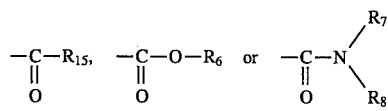

in which:

$R_5$ and $R_6$ represent $C_1$–$C_4$ lower alkyl radicals; and $R_7$ and $R_6$ denote a hydrogen atom or a $C_1$–$C_4$ lower alkyl radical, on condition that they do not simultaneously denote a hydrogen atom.

When Y denotes an oxygen atom, the compounds of formula (I) according to the invention can coexist with their tautomeric form of formula ($I_2$) according to the following equilibrium:

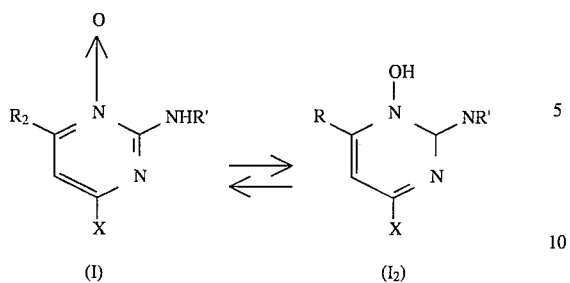

Depending on the nature of the medium, one of the tautomeric forms can be preponderent relative to the other.

The compounds of formula (I) according to the invention may be converted to their cosmetically or pharmaceutically acceptable addition salts with acids, such as the salts with sulphuric, hydrochloric, hydrobromic, phosphoric, acetic, benzoic, salicylic, glycolic, succinic, nicotinic, tartaric, maleic, pamoic, methane-sulphonic, picric and lactic acids, and the like.

Among the compounds of general formula (I), a number of compounds are known per se and have been described as antihypertensive agents or as synthesis intermediates.

They are, in particular, described in U.S. Pat. Nos. 3,464, 987, 3,644,364, 4,013,778 and 4,287,338; French Patent No. 2,087,936; and European Patents EP 058,476 and EP 057, 546; or mentioned in the technical literature (Can. J. Chem. 1984, 62(6), 1176–80; Müller, Ramuz, Helv. Chim., Act. 65 (5), 1982, pages 1454–66).

New compounds according to the present invention correspond to the following formula (I'):

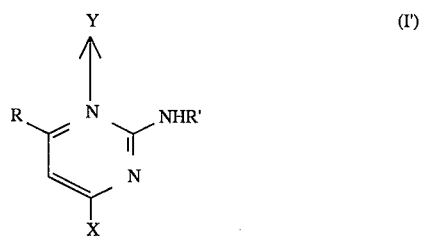

in which:

R, R' and Y have the same meanings stated in the formula (I) above, and X denotes:

(i) a group —$SR_4$, in which $R_4$ denotes a saturated linear or branched $C_1$–$C_{12}$ alkyl radical which can be substituted with a halogen atom or a trifluoromethyl radical, a linear $C_2$–$C_{12}$ alkenyl radical, a $C_3$–$C_{10}$ cycloalkyl radical, a $C_7$–$C_{12}$ aralkyl radical or a phenyl radical optionally substituted with one or two groups which, independently of one another, denote a halogen atom, a $C_1$–$C_6$ alkyl radical, a $C_1$–$C_6$ alkoxy radical or a trifluoromethyl radical;

(ii) a group —$OR_3$ in which $R_3$ has the same meaning as $R_4$, on condition that, when Y denotes an oxygen atom, R an alkyl group and R' denotes a hydrogen atom, $R_3$ does not denote a $C_1$–$C_4$ alkyl radical or a phenyl radical optionally substituted with one or two halogen atoms.

The new compounds of formula (I') can occur in the form of physiologically acceptable addition salts with acids.

The compounds according to the present invention corresponding to the general formula (I) are obtained from a 2-aminopyrimidine 3-oxide derivative substituted at the 6-position, of the following formula:

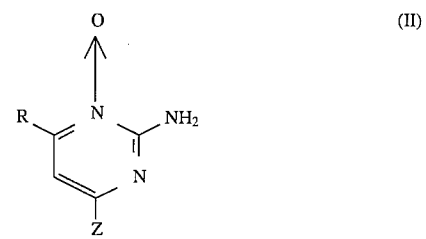

in which:

R has the meaning stated in the general formula (I); and

Z denotes a halogen atom selected from chlorine or bromine, a sulphonate group such as tosylate, brosylate or mesylate or a phenoxy group substituted with electron-attracting groups such as halogen atoms or nitro groups.

The particular compounds according to the invention corresponding to the formula (IA):

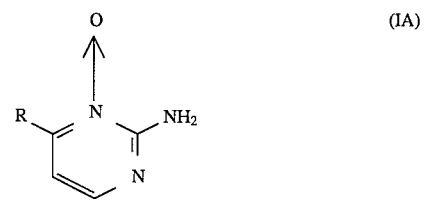

in which R has the meaning stated in the formula (I) above, are obtained by hydrogenolysis of the compounds of formula (II) in which Z more especially denotes a chlorine or bromine atom. The reduction is performed according to the conventional methods described in the technical literature (D. J. Brown, The pyrimidines, Vol. 16, supplement II, Chapter X, 360). The process for preparing them may be represented by the following scheme:

SCHEME A

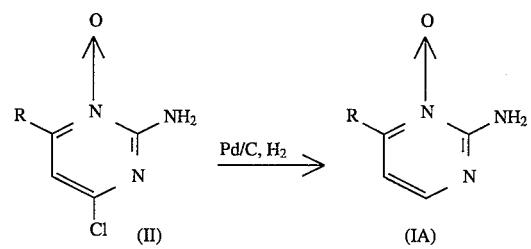

The particular compounds of formula (IB):

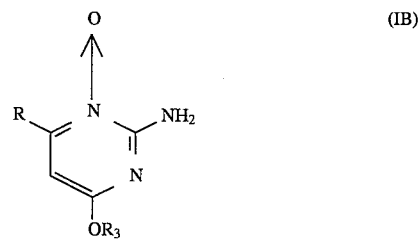

are obtained by reacting a solution of the alcoholate $R_3O^{\ominus}W^{\oplus}$ in which $R_3$ has the same meaning as that stated for the general formula (I) and W denotes an alkali metal such as sodium, potassium or lithium, in the corresponding alcohol, with the compounds of formula (II) in which Z denotes chlorine or bromine or a phenoxy group substituted with electron-attracting groups.

The Williamson method is applied, as described in European Patent EP 57,546, at a temperature of between 40° and 100° C.

The preparation of these compounds may be represented by the following scheme:

SCHEME B

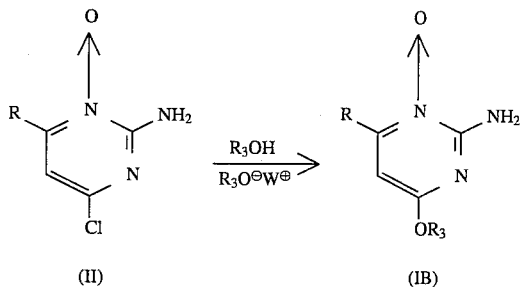

The particular compounds of the following formula (IC):

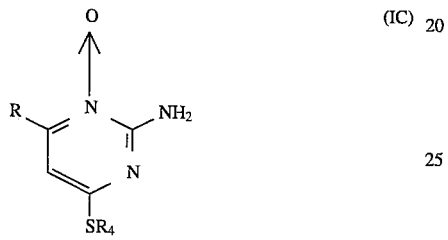

are prepared by reacting the compounds of formula (II) with a thiolate of formula $R_4S^{\ominus}W^{\oplus}$, in which $R_4$ and W have the meanings stated above, in the presence of a solvent selected from ethers, preferably Methyl cellosolve or ethylene glycol dimethyl ether, at a temperature of the order of 50° to 150° C.

The reaction is performed according to the conventional methods of the literature (D. J. Brown, the PYRIMIDINES, Vol. 16, Supplement II, Chapter VI, Section F).

The preparation of these compounds may be represented by the following scheme:

SCHEME C

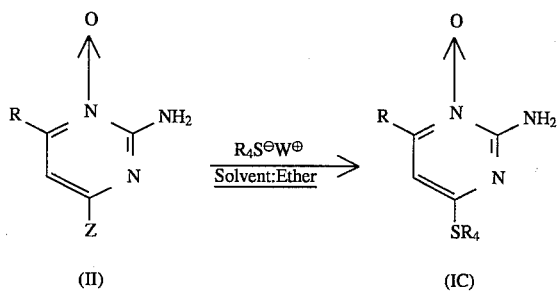

The particular compounds of the following formula (ID):

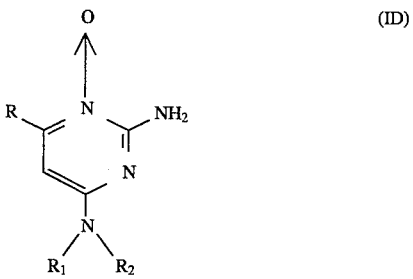

are obtained by reacting an amine

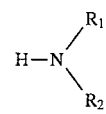

in which $R_1$ and $R_2$ have the same meanings as those stated for the general formula (I), with the compounds of formula (II). The reaction is performed in the presence of a solvent which can be an alcohol, preferably ethanol, or the amine serving as a reactant and at the same time as a solvent, at a temperature of between 20° and 150° C., according to the processes described in U.S. Pat. Nos. 3,644,364 and 3,464,987.

The preparation of these compounds may be represented by the following scheme:

SCHEME D

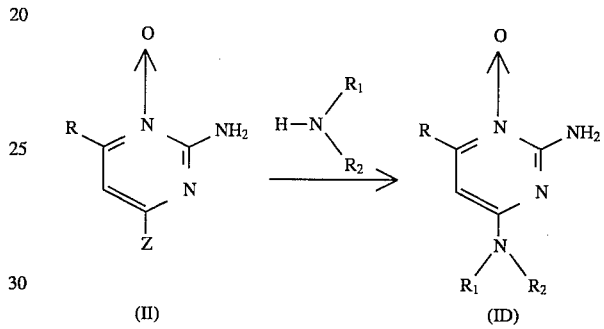

The particular compounds according to the invention of formula (I) in which Y denotes an oxygen atom, obtained according to the different processes described above, may be converted to their O-sulphate homologues by chemical sulphation according to the conventional methods described in the literature (J. Med. Chem. 1983, 26, p. 1791–1793).

The sulphur trioxide/pyridine, sulphur trioxide/triethylamine or sulphur trioxide/ethyldiisopropylamine complexes are used as a sulphating reagent.

The solvents used are preferably dimethylformamide, acetonitrile, chloroform or binary mixtures thereof. The temperature is of the order of 0° to 25° C. and the reaction time varies between 1 hour and 24 hours.

The particular compounds according to the invention of formula (I) in which Y denotes an oxygen atom may be converted to their amide, ureide or carbamate homologues according to the conventional methods described in the literature (J. MARCH, Advanced Organic Chemistry, 3rd edition, p. 370), by the action of an acid chloride, an acid anhydride, a carbamic acid chloride or an alkyl chloroformate, respectively; the reaction is performed in the presence of a tertiary amine such as pyridine.

The compounds thereby obtained, of formula:

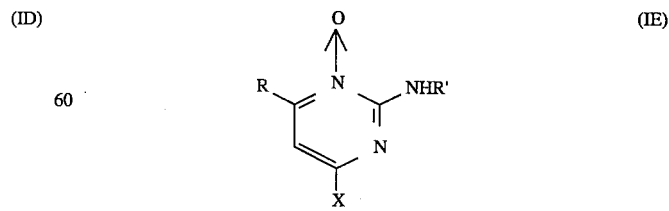

in which R, R' and X have the same meaning as that stated for the formula (I) defined above, are readily hydrolyzable, in an alcoholic potassium hydroxide medium for example, and can give rise once more to their precursors of formula (I) in which R' denotes a hydrogen.

The conversion of the compounds of formula (I) in which Y is oxygen and R' is hydrogen to their O-sulphate, amide, ureide or carbamate homologues may be represented by the following scheme:

SCHEME E

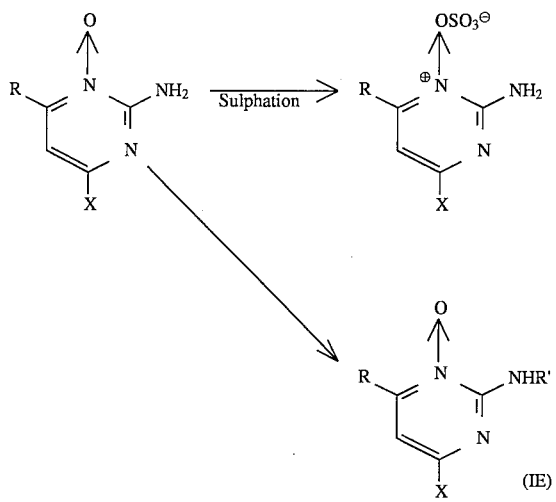

The compounds of formula (IE) according to the invention can constitute intermediates for the synthesis of the oxadiazolopyrimidines of the following formula (III):

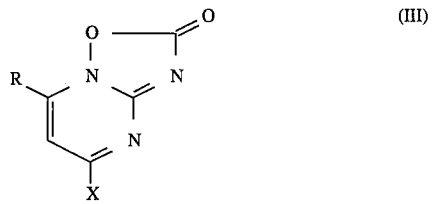

in which R and X have the meaning stated in the general formula (I).

The compounds (III) are obtained by internal cyclization/elimination of the carbamate or ureide derivatives of the formula (IE) according to the methods described in the literature (J. C. MÜLLER, Helvetica Chimica Acta, Vol. 66, 1983, p. 669–672).

The compounds of formula (III) and their salts are new, with the exception of the following compound, namely 2-oxo-2,8-dihydro[1,2,4]oxadiazolo[2,3-a]pyrimidine carbamate which is described in the document (MÜLLER, RAMUZ, Helvetica Chimica Acta 65 (5), 1982, p. 1454–66) and constitute another subject of the invention. They can receive various applications, and in particular in the use for the treatment and prevention of hair loss.

The compositions according to the present invention, containing, in a physiologically acceptable medium, at least one compound corresponding to the formula (I) or one of its physiologically acceptable addition salts with acids, may be applied in the cosmetic or pharmaceutical field, in particular in topical application. They are intended for the treatment and prevention of hair loss, and in particular of pelade, alopecia and also desquamating dermatitis.

These compositions can contain, by way of a physiologically acceptable medium, any medium suitable for topical application, either in cosmetics or in pharmacy, and which is compatible with the active substance.

The compounds according to the invention can be present in this medium either in the dissolved state or in the dispersed state, in particular in micronized form.

The compositions intended for use in pharmacy are presented in the form of an ointment, tincture, cream, pomade, powder, patch, impregnated pad, solution, emulsion or vesicular dispersion, lotion, gel, spray or suspension. They may be either anhydrous or aqueous, depending on the clinical indication.

The compounds according to the invention are present in these pharmaceutical compositions at concentrations of between 0.1 and 10% by weight, and especially between 0.2 and 5% by weight.

The cosmetic compositions are, in particular, intended for use in the form of a lotion, gel, soap, shampoo, aerosol or foam, and contain, in a cosmetically acceptable vehicle, at least one compound of formula (I) or one of its addition salts with acids.

The concentration of these compounds of formula (I) in these compositions is preferably between 0.01 and 5% by weight, and especially between 0.05 and 3% by weight.

The compositions according to the invention can contain different additives customarily used in cosmetics or in pharmacy, and especially active substances such as hydrating agents, for example thiamorpholinone and its derivatives or urea; antiseborrhoeic agents such as S-carboxymethylcysteine, S-benzylcysteamine and their derivatives; and thioxolone.

The compounds according to the invention may be combined with compounds further improving their activity with respect to hair regrowth and/or to retarding its loss, such as, more especially, the following compounds:

nicotinic acid esters including, more especially, $C_1$–$C_6$alkyl nicotinates, and in particular methylnicotinate;

steroidal and non-steroidal anti-inflammatory agents well known in the prior art, and especially hydrocortisone, its salts and its derivatives and niflumic acid;

retinoids, and more especially all-trans-retinoic acid also known as tretinoin, isotretinoin, retinol or vitamin A and its derivatives such as the acetate, palmitate or propionate, motretinide, etretinate and zinc all-trans-retinoate;

antibacterial agents selected, more especially, from macrolides, pyranosides and tetracyclines, and in particular erythromycin;

calcium antagonists such as, more especially, cinnarizine and diltiazem;

hormones such as oestriol or analogues or thyroxine and its salts;

anti-androgens such as oxendolone, spironolactone and diethylstilboestrol; and

OH radical-trapping agents such as dimethyl sulphoxide.

It is also possible to combine with the compounds of the invention, where appropriate mixed with the others, compounds such as diazoxide corresponding to 3-methyl-7-chloro-2H-1,2,4-benzothiadiazine 1,1-dioxide; spiroxasone or 7-(acetylthio)-4',5'-dihydrospiro[androst-4-ene-17, 2'(3'H)-furan]-3-one; phospholipids such as lecithin; linoleic and linolenic acids; salicylic acid and its derivatives described, more especially, in French Patent 2,581,542, and more especially salicylic acid derivatives bearing an alkanoyl group having 2 to 12 carbon atoms at the 5-position of the benzene ring; hydroxy-carboxylic or keto-carboxylic acids and their esters and lactones and their corresponding salts; anthralin or 1,8,9-trihydroxyanthracene; carotenoids; and 5,8,11,14-eicosatetraynoic and 5,8,11-eicosatriynoic acids, their esters and amides.

The compounds according to the invention may also be combined with surfactants including, more especially, those selected from nonionic and amphoteric surfactants.

Among nonionic surfactants, there will be mentioned, more especially, the polyhydroxypropyl ethers described, in particular, in French Patents Nos. 1,477,048, 2,091,516, 2,169,787, 2,328,763 and 2,574,786; oxyethylenated($C_8$–$C_9$alkyl)phenols containing from 1 to 100 moles of ethylene oxide, and preferably 5 to 35 moles of ethylene oxide; and alkylpolyglycosides of formula:

$$C_nH_{2n+1}(C_6H_{10}O_5)_xH \qquad (A)$$

in which n varies from 8 to 15 inclusive and x from 1 to 10 inclusive.

Among amphoteric surfactants, there will be mentioned, more especially, the amphocarboxyglycinates and amphocarboxypropionates defined in the CTFA Dictionary, 3rd edition, 1982, and sold, in particular, under the name MIRANOL® by the company MIRANOL.

The compounds according to the invention may be introduced into vehicles which further improve the activity in respect of regrowth, at the same time possessing advantageous properties from a cosmetic standpoint, such as ternary volatile mixtures of alkylene glycol alkyl ether, especially ($C_1$–$C_4$ alkylene) glycol or dialkylene glycol and preferably ($C_1$–$C_4$ dialkylene) glycol ($C_1$–$C_4$ alkyl) ether, ethyl alcohol and water, the glycol solvent denoting, more especially, ethylene glycol monoethyl ether, propylene glycol monomethyl ether or diethylene glycol monomethyl ether.

The compounds according to the invention may also be introduced into gelled or thickened vehicles, such as essentially aqueous vehicles gelled with heterobiopolysaccharides such as xanthangumor cellulose derivatives, aqueous-alcoholic vehicles gelled with polyhydroxyethyl acrylates or methacrylates or essentially aqueous vehicles thickened, in particular, with polyacrylic acids crosslinked with a polyfunctional agent, such as the Carbopols sold by the company GOODRICH.

These compositions can also contain preservatives, stabilizers, pH regulators, osmotic pressure-modifying agents, emulsifiers, UV-A and UV-B screening agents and antioxidants such as α-tocopherol, butylated hydroxyanisole and butylated hydroxytoluene.

The physiologically acceptable mediumcan consist of water or a mixture of water and a solvent or a mixture of solvents, the solvents being selected from organic solvents which are acceptable from a cosmetic or pharmaceutical standpoint, and selected more especially from $C_1$–$C_4$ lower alcohols such as ethyl alcohol, isopropyl alcohol and tert-butyl alcohol, alkylene glycols and alkylene glycol and dialkylene glycol alkyl ethers such as ethylene glycol monoethyl ether, propylene glycol monomethyl ether and diethylene glycol monomethyl ether. The solvents, if any, are present in proportions of between 1 and 80% by weight relative to the total weight of the composition.

The physiologically acceptable media may be thickened by means of thickening agents customarily used in cosmetics or pharmacy, and heterobiopolysaccharides such as xanthangum, scleroglucans, cellulose derivatives such as cellulose ethers and acrylic polymers, crosslinked or otherwise, may be mentioned more especially.

The thickeners are preferably present in proportions of between 0.1 and 5% by weight, and especially between 0.4 and 3% by weight, relative to the total weight of the composition.

The subject of the invention is also a process for cosmetic treatment of the hair or scalp, consisting in applying thereon at least one composition as defined above, for the purpose of enhancing the appearance of the hair.

Another subject of the invention consists of the use of the composition containing the compounds of formula (I) defined above, for the preparation of a medicinal product having the effect of inducing or stimulating hair growth and retarding its loss.

The treatment consists chiefly in applying the composition as defined above on the alopecic areas of an individual's scalp.

The preferred method of application consists in applying 1 to 2 g of the composition on the alopecic area at the rate of one or two applications per day for 1 to 7 days per week over a period of 1 to 6 months.

The compositions can, in particular, be used in the treatment of pelade, hair loss and desquamating dermatitis.

The examples which follow are intended as illustrations of the invention, no limitation of the latter, however, being implied.

PREPARATION EXAMPLES

Example 1

2-Amino-4-methyl-6-piperidinopyrimidine 3-oxide

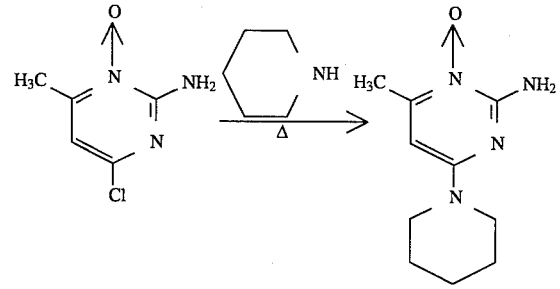

Procedure:

15 g ($9.35\times10^{-2}$ mole) of 2-amino-4-methyl-6-chloropyrimidine 3-oxide are suspended in 150 ml of piperidine. The mixture is heated to 100° C. for 8 hours. After cooling of the reaction medium, the precipitate is filtered off and washed with piperidine and then ethyl ether. It is then added to 35 ml of 10% aqueous sodium hydroxide solution containing 6 g of sodium chloride; the mixture is left stirring for ½ hour and the resulting precipitate is then filtered off and, after drying, is recrystallized in a water/ethanol (80:20) system..

Mass obtained=12.5 g

Yield=64%

M.p. 262° C.

Elemental analysis for $C_{10}H_{16}N_4O$; MW=208

|  | C | H | N | O |
|---|---|---|---|---|
| Calculated | 57.69 | 7.69 | 26.92 | 7.69 |
| Found | 57.76 | 7.73 | 26.81 | 7.71 |

The $^1H$ and $^{13}C$ NMR spectra as well as the mass spectra are in agreement with the structure.

EXAMPLE 2

2-Amino-4-methyl-6-pyrrolidinopyrimidine 3-oxide

Procedure:

In a 250-ml three-necked flask equipped with a magnetic stirrer, a thermometer and a condenser, 9 g ($5.61\times10^{-2}$ mole) of 2-amino-4-methyl-6-chloropyrimidine 3-oxide are suspended in 90 ml of pyrrolidine. The reaction medium is stirred for 2 hours at room temperature, i.e. 25° C. After the mixture has been cooled to 5° C., the precipitate is filtered off on sintered glass. It is washed with 100 ml of acetone and then with 2×100 ml of ethyl ether. Mass obtained=8.85 g.

The precipitate is recrystallized in an acetonitrile/water (95:5) mixture. A precipitate of white scales is obtained.

Mass obtained=4.70 g

Yield=43%

M.p. 260° C. (decomposition)

Elemental analysis for $C_9H_{14}N_4O$; MW=194

|  | C | H | N | O |
| --- | --- | --- | --- | --- |
| Calculated | 55.67 | 7.22 | 28.86 | 8.25 |
| Found | 55.69 | 7.29 | 29.03 | 8.37 |

The $^{13}C$ NMR and mass spectra are in agreement with the structure.

EXAMPLE 3

2-Amino-4-methyl-6-morpholinopyrimidine 3-oxide

Procedure:

In a 100-ml three-necked flask equipped with a magnetic stirrer, a thermometer and a condenser, 5 g ($3.12 \times 10^{-2}$ mole) of 2-amino-4-methyl-6-chloropyrimidine 3-oxide are suspended in 50 ml of morpholine. The reaction medium is stirred for 2 hours at room temperature, i.e. 25°. After the mixture has been cooled to 5°, the precipitate is filtered off on sintered glass. It is washed with 2×50 ml of acetone and then with 2×50 ml of ethyl ether. Mass obtained=9.10 g.

The precipitate is taken up in 90 ml of 10% alcoholic potassium hydroxide. The mixture is stirred for 1 hour and then filtered through a glass sinter packed beforehand with silica. The solution is evaporated to dryness.

The precipitate is recrystallized in an acetonitrile/water (90:10) mixture.

Mass obtained=2.1 g

Yield=35%

M.p. >260° C.

Elemental analysis for $C_9H_{14}N_4O_2$; MW=210

|  | C | H | N | O |
| --- | --- | --- | --- | --- |
| Calculated | 51.43 | 6.66 | 26.67 | 15.24 |
| Found | 51.48 | 6.71 | 26.57 | 15.48 |

The $^{13}C$ NMR and mass spectra are in agreement with the structure.

EXAMPLE 4

2-Amino-4-methyl-6-thiomorpholinopyrimidine 3-oxide

The procedure described in Example 3 is followed, but using thiomorpholine.

Temperature : 25° C.

Time : 2 hours

Recrystallization in acetonitrile/ethanol (90:10)

Yield=42%

M.p. 243° C.

Elemental analysis for $C_9H_{14}N_4OS$; MW=226

|  | C | H | N | O | S |
| --- | --- | --- | --- | --- | --- |
| Calculated | 47.78 | 6.19 | 24.78 | 7.08 | 14.16 |
| Found | 47.88 | 6.25 | 24.86 | 7.22 | 14.03 |

The $^{13}C$ NMR and mass spectra are in agreement with the structure.

EXAMPLE 5

2-Amino-4-methyl-6-(N-methylpiperazino)pyrimidine 3-oxide

The procedure described in Example 3 is followed, using N-methylpiperazine.

Temperature : 30° C.

Time : 18 hours

Recrystallization in an acetonitrile/ethanol (50:50) system

Yield=36%

M.p. 220° C.

Elemental analysis for $C_{10}H_{17}N_5O \cdot \frac{1}{4}H_2O$; MW=223

|  | C | H | N | O |
| --- | --- | --- | --- | --- |
| Calculated | 52.75 | 7.69 | 30.77 | 8.79 |
| Found | 52.90 | 7.66 | 30.95 | 8.83 |

Calculated with 0.25 mol $H_2O$

The $^{13}C$ NMR and mass spectra are in agreement with the structure.

EXAMPLE 6

2-Amino-4-methyl-6-diethylaminopyrimidine 3-oxide

Procedure:

In a 250-ml three-necked flask equipped with a magnetic stirrer, a thermometer and a condenser, 10 g ($6.24 \times 10^{-2}$ mole) of 2-amino-4-methyl-6-chloropyrimidine 3-oxide are suspended in 70 ml of ethanol. 10 equivalents of diethylamine, i.e. 60 ml, are added at room temperature. The reaction medium is heated to 50° C. for 24 hours. It is cooled to 5° C. and 70 ml of 10% alcoholic potassium hydroxide are then added.

The mixture is stirred for 1 hour. It is filtered through a glass sinter packed beforehand with silica. The solution is evaporated to dryness. Mass obtained=9.5 g.

The precipitate is recrystallized in acetonitrile. Mass=7.15 g.

Yield=58%

M.p. 188° C.

Elemental analysis for $C_9H_{16}N_4O$; MW=196

|  | C | H | N | O |
| --- | --- | --- | --- | --- |
| Calculated | 55.10 | 8.16 | 28.57 | 8.16 |
| Found | 54.93 | 8.13 | 28.77 | 8.40 |

The $^{13}C$ NMR and mass spectra are in agreement with the structure.

EXAMPLE 7

2-Amino-4-methyl-6-dimethylaminopyrimidine 3-oxide

The procedure described in Example 6 is followed, using dimethylamine.

Temperature : 25° C.
Time : 3 hours
Recrystallization in an acetonitrile/water (90:10) system
Yield=67%
M.p. 222° C.
Elemental analysis for $C_7H_{12}N_4O$; MW=168

|  | C | H | N | O |
|---|---|---|---|---|
| Calculated | 50.00 | 7.14 | 33.33 | 9.52 |
| Found | 49.99 | 7.16 | 33.29 | 9.64 |

The $^{13}C$ and $^1H$ NMR and mass spectra are in agreement with the structure.

EXAMPLE 8

2-Amino-4-methyl-6-diallylaminopyrimidine 3-oxide
Procedure:

In a 100-ml three-necked flask equipped with a magnetic stirrer, a thermometer and a condenser, 5 g ($3.12 \times 10^{-2}$ mole) of 2-amino-4-methyl-6-chloropyrimidine 3-oxide are suspended in 50 ml of ethanol. 2.2 equivalents of diallylamine, i.e. 6.7 g, are added at room temperature. The reaction medium is heated at 60° C. for 24 hours.

The mixture is cooled to 5° C. and the precipitate corresponding to the remainder of the 2-amino-4-methyl-6-chloropyrimidine 3-oxide is filtered off. The solution is evaporated to dryness. Ethanolic hydrogen chloride is added until the pH is acid. On adding ethyl ether, 2-amino-4-methyl-6-diallylaminopyrimidine 3-oxide monohydrochloride is precipitated.

This precipitate is recrystallized an in acetone/ethanol mixture.

Mass obtained=1 g
Yield=12%
M.p. 166° C.

The derivative is isolated in the form of its hydrochloride.
Elemental analysis for $C_{11}H_{17}N_4OCl$; MW=256.5

|  | C | H | N | O | Cl |
|---|---|---|---|---|---|
| Calculated | 51.45 | 6.63 | 21.83 | 6.23 | 13.84 |
| Found | 51.56 | 6.65 | 21.92 | 6.38 | 13.72 |

The NMR and mass spectra are in agreement with the structure.

EXAMPLE 9

2-Amino-4-methyl-6-(n-butylamino)pyrimidine 3-oxide
The procedure described in Example 2 is followed, using n-butylamine.
Temperature : 55° C.
Time : 18 hours
Recrystallization in an acetonitrile/water (70:30) system
Yield=49%
M.p. 216° C.

Elemental analysis for $C_9H_{16}N_4O$; MW=196

|  | C | H | N | O |
|---|---|---|---|---|
| Calculated | 55.10 | 8.16 | 28.57 | 8.16 |
| Found | 54.91 | 8.22 | 28.72 | 8.25 |

The $^1H$ NMR and mass spectra are in agreement with the structure.

EXAMPLE 10

2-Amino-4-methyl-6-benzylaminopyrimidine 3-oxide
The procedure described in Example 2 is followed, using benzylamine.
Temperature : 60° C.
Time : 6 house
Recrystallization in a water/ethanol (75:25) system
Yield=53%
M.p. 226° C.
Elemental analysis for $C_{12}H_{14}N_4O$; MW=230

|  | C | H | N | O |
|---|---|---|---|---|
| Calculated | 62.60 | 6.09 | 24.35 | 6.95 |
| Found | 62.69 | 6.02 | 24.43 | 7.06 |

The $^1H$ NMR and mass spectra are in agreement with the structure.

EXAMPLE 11

2-Ethoxycarbonylamino-4-methyl-6-piperidinopyrimidine 3-oxide

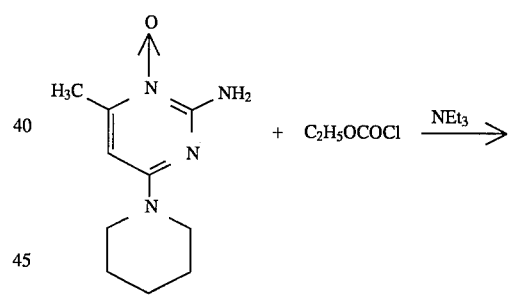

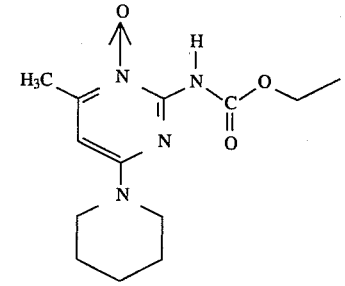

By the action of ethyl chloroformate on 2-amino-4-methyl-6-piperidinopyrimidine 3-oxide in the presence of triethylamine, the expected ethyl carbamate is obtained.

Procedure:

In a 50-ml three-necked flask equipped with a magnetic stirrer, a thermometer and a dropping funnel, 2 g ($1.25 \times 10^{-2}$ mole) of 2-amino-4-methyl-6-piperidinopyrimidine 3-oxide are suspended in 20 ml of dichloromethane dried beforehand over a molecular sieve. 1 equivalent of triethylamine, i.e. 1.35 ml, is added. The reaction medium is cooled to 0° C. and 1 equivalent of ethyl chloroformate, i.e. 1.05 g, is added dropwise. The mixture is allowed to return to room temperature (25° C.) and is stirred for 2 hours.

10 ml of water are added to the reaction medium. The organic phase is extracted with:

10 ml of 1% hydrochloric acid 10 ml of 1% sodium carbonate solution

2×10 ml of water and then dried over sodium sulphate.

After filtration through paper, the solution is evaporated. A white precipitate is obtained.

Mass obtained=2 g

This precipitate is recrystallized in 45 ml of water.

Mass obtained=1.60 g

Yield=60%

M.p. 134° C.

Elemental analysis for $C_{13}H_{20}N_4O_3$; MW=280

|  | C | H | N | O |
|---|---|---|---|---|
| calculated | 55.7 | 17.14 | 20.00 | 17.14 |
| Found | 55.80 | 7.18 | 20.09 | 17.05 |

The $^{13}C$ NMR and mass spectra are in agreement with the structure.

EXAMPLE 12

2-Acetamido-4-methyl-6-dimethylaminopyrimidine 3-oxide

Following the procedure described in Example 11, acetyl chloride is reacted in the presence of triethylamine with 2-amino-4-methyl-6-dimethylaminopyrimidine 3-oxide.

Temperature : 25° C.

Time : 2 hours

Recrystallization in ethyl acetate/methanol (50:50)

Yield=10%

M.p. 208° C.

Elemental analysis for $C_9H_{14}N_4O_2$; MW=210

|  | C | H | N | O |
|---|---|---|---|---|
| Calculated | 51.43 | 6.67 | 26.67 | 15.24 |
| Found | 51.32 | 6.66 | 26.66 | 15.36 |

The $^{13}C$ NMR and mass spectra are in agreement with the structure.

EXAMPLE 13

7-Methyl-2-oxo-5-pyrrolidino-2H-[1,2,4]oxadiazolo[2,3-a]-pyrimidine

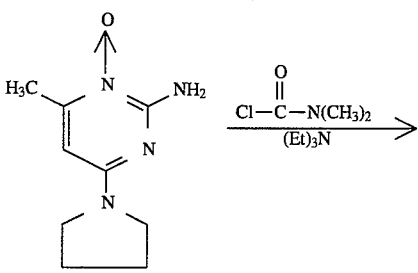

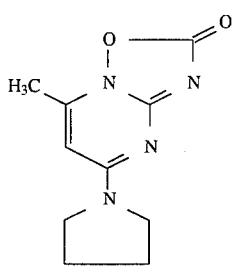

Procedure:

In a 50-ml three-necked flask equipped with a magnetic stirrer, a thermometer and a dropping funnel, 2 g (1.25×10$^{-2}$ mole) of 2-amino-4-methyl-6-pyrrolidinopyrimidine 3-oxide are suspended in 20 ml of dichloromethane dried beforehand over a molecular sieve. 2 equivalents of triethylamine, i.e. 2.9 ml, are added. The reaction medium is cooled to 0° C. 2 equivalents of dimethylcarbamoyl chloride, i.e. 2.2 g, are added dropwise. The mixture is allowed to return to room temperature (25°) and is stirred for 2 hours.

The mixture is cooled to 0° C. and the precipitate corresponding to triethylamine hydrochloride is then filtered off. The solution is evaporated to dryness. The solid obtained is taken up in ethanol. After 1 hour's stirring, the precipitate is filtered off. This precipitate is recrystallized in ethanol.

Mass obtained=0.5 g

Yield=23%

M.p. 255° C. (decomposition)

Elemental analysis for $C_{10}H_{12}N_4O_2 \cdot \frac{1}{5}H_2O$; MW=220

|  | C | H | N | O |
|---|---|---|---|---|
| Calculated | 53.6 | 65.54 | 25.05 | 15.74 |
| Found | 53.96 | 5.51 | 25.25 | 15.66 |

The $^1H$ NMR and mass spectra are in agreement with the expected structure.

EXAMPLE 14

2-Amino-4-methyl-6-methoxypyrimidine 3-oxide

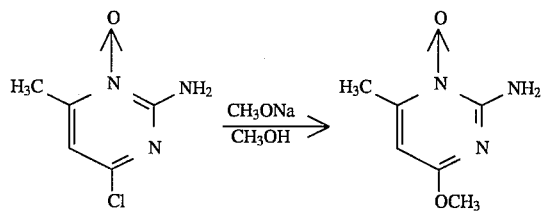

10 g of sodium are dissolved in 750 ml of methanol. 50 g of 2-amino-4-methyl-6-chloropyrimidine 3-oxide are added and the reaction medium is brought to reflux for 4 hours. The solvent is evaporated off and the mixture is dissolved in 250 ml of water and 30 ml of concentrated hydrochloric acid, filtered and then alkalinized by adding sodium hydroxide. The white precipitate obtained is recrystallized in water.

Yield=43%

M.p. 210° C.

Elemental analysis for $C_6H_9N_3O_2 \cdot 0.15H_2O$; MW=155

|  | C | H | N | O |
|---|---|---|---|---|
| Calculated | 45.66 | 5.90 | 26.63 | 21.81 |
| Found | 45.77 | 5.93 | 26.56 | 21.84 |

The $^{13}C$ NMR and mass spectra are in agreement with the expected structure.

EXAMPLE 15

2-Amino-4-methyl-6-ethoxypyrimidine 3-oxide

The procedure described in Example 14 is followed, using ethanol.

Temperature : 80° C.

Time : 4 hours

After the reaction mixture is taken to dryness and ether is added, the precipitate obtained is filtered off. The mother liquors are evaporated off and the product is precipitated with acetone. The white precipitate obtained is recrystallized in an acetone/water mixture.

Yield=25%

M.p. 155° C.

Elemental analysis for $C_7H_{11}N_3O_2$; MW=169

|  | C | H | N | O |
|---|---|---|---|---|
| Calculated | 49.70 | 6.51 | 24.85 | 18.93 |
| Found | 49.34 | 6.6 | 24.63 | 18.69 |

The $^1H$ and $^{13}C$ NMR and mass spectra are in agreement with the expected structure.

EXAMPLE 16

2-Amino-4-methyl-6-butyloxypyrimidine 3-oxide

The procedure described in Example 14 is followed, using butanol.

Temperature : 118° C.

Time : 4 hours

Recrystallization in a petroleum ether/acetone mixture

Yield=34%

M.p. 137° C.

Elemental analysis for $C_9N_{15}O_2$; MW=197

|  | C | H | N | O |
|---|---|---|---|---|
| Calculated | 54.82 | 7.61 | 21.32 | 16.24 |
| Found | 54.74 | 7.65 | 21.20 | 16.41 |

The $^1H$ NMR and mass spectra are in agreement with the expected structure.

EXAMPLE 17

2-Amino-4-methyl-6-(1-methylethyloxy)pyrimidine 3-oxide

The procedure described in Example 14 is followed, but using isopropanol.

Temperature : refluxing

Time : 48 hours

Recrystallization in an acetonitrile/water (98:2) mixture

Yield=10%

M.p. 190° C.

Elemental analysis for $C_8H_{13}N_3O_2$; MW=183

|  | C | H | N | O |
|---|---|---|---|---|
| Calculated | 52.46 | 7.10 | 22.95 | 17.49 |
| Found | 52.44 | 7.20 | 22.92 | 17.58 |

The $^1H$ NMR and mass spectra are in agreement with the expected structure.

EXAMPLE 18

2-Amino-4-methyl-6-(2,2-dimethylpropyloxy)pyrimidine 3-oxide 0.32 g of sodium is dissolved in 50 ml of 2,2-dimethyl-1-propanol in the heated state. 2 g (0.0125 mole) of 2-amino-4-methyl-6-chloropyrimidine 3-oxide are added and the reaction medium is brought to 105° C. for 22 hours. The mixture, still hot, is poured into 300 ml of 10% aqueous sodium hydroxide solution. The product is extracted with ethyl acetate and the organic phase is dried with sodium sulphate. It is concentrated and a brown oil is obtained. The latter is filtered on silica gel using an elution gradient with ethyl acetate and methanol. After evaporation, a solid crude product is obtained, which is recrystallized in an acetonitrile/water (98:2) mixture.

Yield=11%

M.p. 213° C.

Elemental analysis for $C_{10}H_{17}N_3O_2$; MW=211

|  | C | H | N | O |
|---|---|---|---|---|
| Calculated | 56.87 | 8.06 | 19.90 | 15.16 |
| Found | 56.74 | 8.04 | 19.80 | 15.15 |

The $^1H$ NMR and mass spectra are in agreement with the expected structure.

EXAMPLE 19

2-Amino-4-methyl-6-(1-cyclohexylmethyloxy)pyrimidine 3-oxide

The procedure described in Example 14 is followed, using cyclohexylmethanol.

Temperature : 85° C.

Time : 5 hours

Recrystallization in an acetonitrile/water (98:2) mixture

Yield=30%

M.p. 161° C.

Elemental analysis for $C_{12}H_{19}N_3O_2 \cdot 0.1H_2O$; MW=237

|  | C | H | N | O |
|---|---|---|---|---|
| Calculated | 60.25 | 8.04 | 17.57 | 14.13 |
| Found | 69.26 | 8.05 | 17.60 | 14.10 |

The $^1H$ NMR and mass spectra are in agreement with the expected structure.

EXAMPLE 20

2-Amino-4-methyl-6-(5-hexenyloxy)pyrimidine 3-oxide

The procedure described in Example 14 is followed, using 5-hexen-1-ol.

Temperature : 85° C.

Time : 3 hours 15 minutes

Recrystallization in acetonitrile

Yield=27%

M.p. 103° C.

Elemental analysis for $C_{11}H_{17}N_3O_2 \cdot 0.1H_2O$; MW=223

|  | C | H | N | O |
|---|---|---|---|---|
| Calculated | 58.66 | 7.65 | 18.66 | 15.01 |
| Found | 58.68 | 7.65 | 18.52 | 14.93 |

The $^1$H NMR and mass spectra are in agreement with the expected structure.

EXAMPLE 21

2-Amino-4-methyl-6-benzyloxvpyrimidine 3-oxide

The procedure described in Example 14 is followed, using benzyl alcohol.

Temperature : 83° C.

Time : 2 hours 30 minutes

Recrystallization in an acetonitrile/water (98:2) mixture

Yield=45%

M.p. 188° C.

Elemental analysis for $C_{12}H_{13}N_3O_2$; MW=231

|  | C | H | N | O |
|---|---|---|---|---|
| Calculated | 62.33 | 5.62 | 18.18 | 13.85 |
| Found | 62.40 | 5.59 | 18.06 | 13.89 |

The $^1$H NMR and mass spectra are in agreement with the expected structure.

EXAMPLE 22

2-Amino-4-methyl-6-(2,4-dimethylphenyloxy)pyrimidine 3-oxide

The procedure described in Example 14 is followed, using 2,4-dimethylphenol.

Temperature : 75° C.

Time : 4 hours

Recrystallization in an acetonitrile/water (95:5) mixture

Yield=60%

M.p. 214° C.

Elemental analysis for $C_{13}H_{15}N_3O_2$; MW=245

|  | C | H | N | O |
|---|---|---|---|---|
| Calculated | 63.67 | 6.12 | 17.14 | 13.06 |
| Found | 63.60 | 6.16 | 17.16 | 13.19 |

The $^{13}$C and $^1$H NMR and mass spectra are in agreement with the expected structure.

EXAMPLE 23

2-Amino-4-methyl-6-methylthiopyrimidine 3-oxide

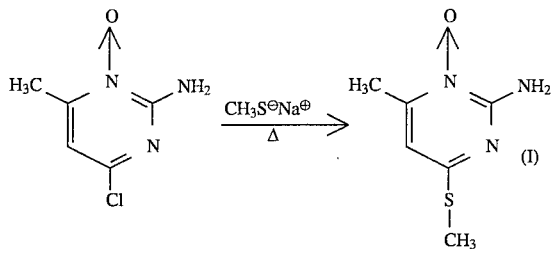

The compound (I) is obtained by the action of sodium methylthiolate in the heated state on 2-amino-4-methyl-6-chloropyrimidine 3-oxide.

Procedure:

5 g ($3.12 \times 10^{-2}$ mole) of 2-amino-4-methyl-6-chloropyrimidine 3-oxide are introduced into 75 ml of 1,2-dimethoxyethane; 5.46 g ($7.81 \times 10^{-2}$ mole) of sodium methylthiolate are added and the mixture is then brought to reflux until the starting substrate has disappeared ($t_{reaction}$=55 hours). After filtration of the reaction medium, the precipitate obtained is dissolved in methanol and treated with ethanolic hydrogen chloride to pH 2; the hydrochloride of the compound (I) is isolated and the associated base is then liberated by adding a 30% solution of sodium methylate in methanol; after the salts have been removed by precipitation with ethyl ether, the resulting filtrate is evaporated to dryness and the product is then recrystallized in an acetonitrile/ethanol (70:30) system. 1.55 g of the compound (I) are obtained.

Yield=29%

M.p. 172° C.

Elemental analysis for $C_6H_9N_3OS$; MW=171

|  | C | H | N | O | S |
|---|---|---|---|---|---|
| Calculated | 42.10 | 5.26 | 24.56 | 9.35 | 18.71 |
| Found | 42.17 | 5.31 | 24.65 | 9.45 | 18.47 |

The $^{13}$C NMR and mass spectra are in agreement with the expected structure.

EXAMPLE 24

2-Amino-4-methyl-6-ethylthiopyrimidine 3-oxide 5 g ($3.12 \times 10^{-2}$ mole) of 2-amino-4-methyl-6-chloropyrimidine 3-oxide are suspended in 75 ml of 1,2-dimethoxyethane; 3.92 g ($4.68 \times 10^{-2}$ mole) of sodium ethyl thiolate are added and the mixture is then brought to reflux until the starting substrate has disappeared ($t_{reaction}$=18 hours). The precipitate originating from the reaction medium is stirred in suspension in 30 ml of water and then filtered off, dried and recrystallized in acetonitrile. 2.1 g of the expected compound are obtained.

Yield=36%

M.p. 152° C.

Elemental analysis for $C_7H_{11}N_3OS$; MW=185

|  | C | H | N | O | S |
|---|---|---|---|---|---|
| Calculated | 45.40 | 5.94 | 22.70 | 8.65 | 17.29 |
| Found | 45.33 | 5.95 | 22.82 | 8.78 | 17.32 |

The $^1$H NMR and mass spectra are in agreement with the expected structure.

EXAMPLE 25

2-Amino-4-methylpyrimidine 3-oxide

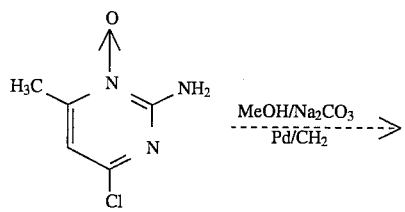

15 g of 2-amino-4-methyl-6-chloropyrimidine 3-oxide, 11 g of sodium carbonate and 2.4 g of palladium/charcoal (10% palladium) are mixed in 1 liter of methanol. The mixture is subjected to hydrogenolysis in a PARR apparatus under $2 \times 10^5$ Pa for 2 hours 30 minutes. The reaction medium is filtered and the solvent is then evaporated off. The precipitate is extracted with boiling ethyl acetate.

Yield=20%

M.p. 145° C.

Elemental analysis for $C_5H_7N_3O$; MW=125

|  | C | H | N | O |
|---|---|---|---|---|
| Calculated | 48.00 | 5.6 | 33.6 | 12.8 |
| Found | 47.97 | 5.6 | 33.7 | 12.87 |

The $^{13}$C NMR and mass spectra are in agreement with the expected structure.

EXAMPLE 26

Internal salt of 2-amino-4-methyl-6-dimethylamino-3-sulphooxypyrimidinium hydroxide

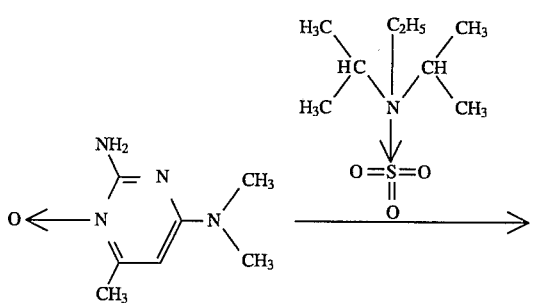

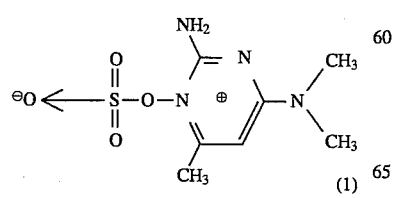

0.2 ml (0.003 mole) of chlorosulphonic acid is added with stirring to a solution, cooled in ice, of 1.03 ml (0.006 mole) of N,N-diisopropylethylamine in 8 ml of chloroform. After 30 minutes have elapsed, 0.252 g (0.0015 mole) of 2-amino-4-methyl-6-dimethylaminopyrimidine 3-oxide is added and the mixture is maintained for 2 hours at between 0° and 5° C. under nitrogen. The white precipitate which has formed is filtered off and then washed with a little chloroform.

After recrystallization in a dimethylformamide/water mixture, 0.11 g of the compound (1) is obtained, the latter decomposing at 250° C. The yield is 30%.

Elemental analysis for $C_7H_{12}N_4O_4S$; MW=248

|  | C | H | N | O | S |
|---|---|---|---|---|---|
| Calculated | 33.88 | 4.84 | 22.58 | 25.80 | 12.90 |
| Found | 33.90 | 4.86 | 22.62 | 25.82 | 12.81 |

Mass spectrum : in agreement

EXAMPLE 27

Internal salt of 2-amino-4-methyl-6-pyrrolidino-3-sulfooxypyrimidinium hydroxide

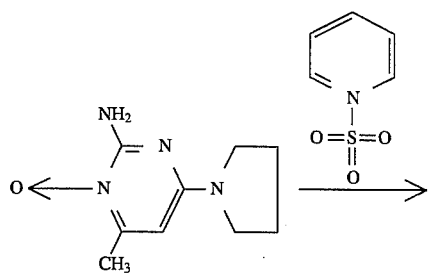

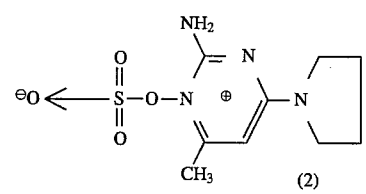

0.32 g (0.002 mole) of a sulphur trioxide pyridine complex is added with stirring to a suspension of 0.194 g (0.001 mole) of 2-amino-4-methyl-6-pyrrolidinopyrimidine 3-oxide, and the mixture is maintained at room temperature for 3 hours. The solution obtained is diluted with 15 g of ice-cold water. The white precipitate is filtered off and then washed with a little ice-cold water.

After recrystallization in a dimethylformamide/water mixture, 0.085 g of the compound (2) is obtained, the latter decomposing at 260° C.

The yield is 31%.

Elemental analysis for $C_9H_{14}N_4O_4S$; MW=274

|  | C | H | N | O | S |
|---|---|---|---|---|---|
| Calculated | 39.42 | 5.11 | 20.44 | 23.36 | 11.68 |
| Found | 39.35 | 5.16 | 20.33 | 23.36 | 11.61 |

Mass spectrum : in agreement

EXAMPLE 28

Internal salt of 2-amino-4-methyl-6-piperidino-3-sulfooxypyrimidinium hydroxide

The procedure described in Example 27 is followed, using 2-amino-4-methyl-6-piperidinopyrimidine 3-oxide.

The product obtained, recrystallized in a dimethylformamide/water mixture, is a monohydrate which decomposes at 184° C.

The yield is 73%.
Elemental analysis for $C_{10}H_{18}N_4O_5S$; MW=306

|  | C | H | N | O | S |
|---|---|---|---|---|---|
| Calculated | 39.21 | 5.88 | 18.30 | 26.14 | 10.46 |
| Found | 39.27 | 6.08 | 18.48 | 26.02 | 10.44 |

Mass spectrum : in agreement
$^1$H NMR spectrum : in agreement

EXAMPLE 29

Internal salt of 2-amino-4-methyl-6-morpholino-3-sulfooxypyrimidinium hydroxide

The procedure described in Example 26 is followed, using 2-amino-4-methyl-6-morpholinopyrimidine 3-oxide.

The reaction time is 3 hours and the temperature is maintained at between 5° and 10° C.

The product obtained, recrystallized in a dimethylformamide/water mixture, decomposes at 250° C.

The yield is 56%.
Elemental analysis for $C_9H_{14}N_4O_5S$; MW=290

|  | C | H | N | O | S |
|---|---|---|---|---|---|
| Calculated | 37.24 | 4.83 | 19.31 | 27.59 | 11.03 |
| Found | 37.29 | 4.81 | 19.39 | 27.83 | 10.96 |

Mass spectrum : in agreement

EXAMPLE 30

Internal salt of 2-amino-4-methyl-6-thiomorpholino-3-sulfooxypyrimidinium hydroxide The procedure described in Example 26 is followed, using 2-amino-4-methyl-6-thiomorpholinopyrimidine 3-oxide.

The reaction time is 1 hour 30 minutes.

The product obtained, recrystallized in a dimethylformamide/water mixture, decomposes above 260° C.

The yield is 74%.
Elemental analysis for $C_9H_{14}N_4O_4S_2$; MW=306

|  | C | H | N | O | S |
|---|---|---|---|---|---|
| Calculated | 35.29 | 4.57 | 18.30 | 20.91 | 20.91 |
| Found | 35.15 | 4.50 | 18.35 | 21.10 | 20.88 |

Mass spectrum : in agreement

EXAMPLE 31

Internal salt of 2-amino-4-methyl-6-(4-methylpiperazino)-3-sulfooxypyrimidinium hydroxide The procedure described in Example 26 is followed, using 2-amino-4-methyl-6-(4-methylpiperazino)pyrimidine 3-oxide.

The reaction time is 3 hours.

The product obtained, recrystallized in a dimethylformamide/water mixture, decomposes at 265° C.

The yield is 20%.
Elemental analysis for $C_{10}H_{17}N_5O_4S.0.15H_2O$; MW=303

|  | C | H | N | O | S |
|---|---|---|---|---|---|
| Calculated | 39.27 | 5.65 | 22.91 | 21.68 | 10.47 |
| Found | 39.18 | 5.72 | 23.01 | 21.68 | 10.46 |

Mass spectrum : in agreement

EXAMPLE 32

Internal salt of 2-amino-4-methyl-6-methoxy-3-sulfooxypyrimidinium hydroxide

The procedure described in Example 26 is followed, using 2-amino-4-methyl-6-methoxypyrimidine 3-oxide.

The reaction time is 1 hour 30 minutes.

The yield of crude product is 60%.

Mass spectrum : in agreement

EXAMPLE 33

Internal salt of 2-amino-4-methyl-6-ethoxy-3-sulfooxypyrimidinium hydroxide 0.2 ml (0.003 mole) of chlorosulphonic acid is added with stirring to a solution, cooled in ice, of 1.03 ml (0.006 mole) of N,N-diisopropylethylamine in 8 ml of chloroform. After 30 minutes have elapsed, 0.253 g (0.0015 mole) of 2-amino-4-methyl-6-ethoxypyrimidine 3-oxide is added and the mixture is maintained for 2 hours at between 0° C. and 5° C. under nitrogen. The solvent is evaporated off. The residue, taken up in a little water, gives rise to the crystallization of a white product, which is filtered off and dried.

The yield of crude product is 25%.

Mass spectrum : in agreement

EXAMPLE 34

2-Amino-4,5-tetramethylene-6-piperidinopyrimidine 3-oxide

1st part:

Preparation of 2-amino-4,5-tetramethylene-6-hydroxypyrimidine.

In a three-necked flask equipped with a condenser, a thermometer and an argon inlet, 2.15 g ($9.35 \times 10^{-2}$ mole) of sodium are dissolved in 70 ml of absolute ethanol, and 8.95 g ($9.37 \times 10^{-2}$ mole) of guanidinium chloride are then added in large portions while the temperature is maintained at 25° C.

16.66 ml of 90% pure ethyl 2-cyclohexanonecarnoxylate ($9.37 \times 10^{-2}$ mole), introduced beforehand into a dropping funnel, are then run in gradually; the run-in time is 20 min and the temperature of the exothermic reaction rises to 45° C.

When the reaction medium has returned to room temperature, the precipitate is filtered off and washed copiously with water to remove the sodium chloride and then with ethanol; the crude mass thereby obtained is recrystallized in water.

Recrystallized mass: 11.84 g
Yield=76.3%
Analyses:
M.p. 300° C.

Elemental analysis for $C_8H_{11}N_3O \cdot 0.1H_2O$; MW=165

|  | C | H | N | O |
|---|---|---|---|---|
| Calculated | 57.55 | 6.65 | 25.18 | 10.55 |
| Found | 57.57 | 6.73 | 25.09 | 10.56 |

The $^1H$ NMR and mass spectra are in agreement with the expected structure.

2nd part:

Preparation of 2-amino-4,5-tetramethylene-6-chloropyrimidine.

10 g ($6 \times 10^{-2}$ mole) of 2-amino-4,5-tetramethylene-6-hydroxypyrimidine in 100 ml of phosphorus oxychloride are introduced into a 250-ml three-necked flask equipped with a thermometer, a condenser surmounted by a calcium chloride guard tube and a magnetic stirrer.

The medium is heated to 100° C. for ½ hour and then allowed to return to room temperature. The phosphorus oxychloride is evaporated off; the oil obtained is poured slowly into 6.6% aqueous ammonia solution (300 ml) while the temperature is maintained below 10° C.

The mixture is stirred for ½ hour and the white precipitate obtained is filtered off and washed with water to neutrality.

The crude mass thereby recovered is recrystallized in ethanol.

Crystallized mass=4 g
Yield=36.4%
Analyses:
M.p. 207° C.
Elemental analysis for $C_8H_{10}N_3Cl$; MW=183.5

|  | C | H | N | Cl |
|---|---|---|---|---|
| Calculated | 52.32 | 5.45 | 22.89 | 19.34 |
| Found | 52.27 | 5.49 | 22.98 | 19.46 |

The $^1H$ NMR and mass spectra are in agreement with the expected structure.

3rd part:

Preparation of 2-amino-4,5-tetramethylene-6-chloropyrimidine 3-oxide

In a one-liter three-necked flask equipped with a thermometer and a magnetic stirrer, 30 g ($16.34 \times 10^{-2}$ mole) of 2-amino-4,5-tetramethylene-6-chloropyrimidine are suspended in 600 ml of methanol; 76.2 g (1.5 equivalents) of 55% pure meta-chloroperbenzoic acid are then added while the temperature is maintained at 5° C.

The mixture is then left stirring for 4 hours at room temperature (25° C.).

The reaction medium is filtered and the precipitate isolated is washed with cold methanol and then with ethyl ether.

Mass obtained=28.5 g
Yield=87%
Analyses:
M.p. 188° C.
Elemental analysis for $C_8H_{10}ClN_3O$; MW=199.5

|  | C | H | N | O | Cl |
|---|---|---|---|---|---|
| Calculated | 42.12 | 5.01 | 21.05 | 8.02 | 17.79 |
| Found | 48.07 | 5.05 | 21.09 | 7.95 | 17.85 |

The $^1H$ NMR and mass spectra are in agreement with the expected structure.

4th part:

Preparation of 2-amino-4,5-tetramethylene-6-piperidinopyrimidine 3-oxide

Procedure:

10 g ($5 \times 10^{-2}$ mole) of 2-amino-4,5-tetramethylene-6-chloropyrimidine 3-oxide are introduced into 100 ml of piperidine; the reaction medium is heated to reflux for 8 hours, cooled to room temperature and then filtered on sintered glass. A refrigerated solution of 30 cc of water in which 2 g of sodium hydroxide and 3 g of sodium chloride have been dissolved is added in large portions to the precipitate obtained. The mixture is stirred for 1 hour and the product is filtered off and washed with water to neutrality; the white crystals are recrystallized in a water/ethanol (50:50) mixture.

Mass obtained=5.4 g
Yield=43.5%
Analyses:
M.p. 178° C.
Elemental analysis for $C_{13}H_{20}N_4O \cdot 0.3H_2O$; MW=248

|  | C | H | N | O |
|---|---|---|---|---|
| Calculated | 61.56 | 5.13 | 22.09 | 8.21 |
| Found | 62.02 | 8.11 | 22.19 | 8.24 |

The $^1H$ NMR and mass spectra are in agreement with the expected structure.

EXAMPLE 35

Preparation of 2-amino-4,5-tetramethylene-6-butoxypyrimidine 3-oxide

Procedure:

In a three-necked flask equipped with a condenser, a thermometer and an argon inlet, 1.72 g ($7.5 \times 10^{-2}$ mole) of sodium are added to 100 ml of anhydrous butanol, and the mixture is stirred for ¾ hour while allowing the exothermic effect linked to the formation of sodium butylate to develop. 10 g ($5 \times 10^{-2}$ mole) of 2-amino-4,5-tetramethylene-6-chloropyrimidine 3-oxide are then added in large portions and the mixture is thereafter heated to reflux of the butanol for 1 hour.

After cooling of the reaction medium, the latter is filtered and the filtrate is adjusted to neutrality by adding ethanolic hydrogen chloride; the sodium chloride is removed, the organic phase is then washed with 30 ml of distilled water and evaporated to dryness and the resulting oily residue is precipitated by adding ethyl ether. The mixture is stirred in a bath of ice-cold water for ½ hour and then filtered.

The crude mass obtained (9 g) is recrystallized in an acetonitrile/water (50:50) mixture; 4.65 g of the pure compound are thereby recovered.

Yield=39%
Analyses:
M.p. 166° C.
Elemental analysis for $C_{12}H_{19}N_3O_2$; MW=237

|  | C | H | N | O |
| --- | --- | --- | --- | --- |
| Calculated | 60.76 | 8.02 | 17.72 | 13.50 |
| Found | 60.76 | 8.06 | 17.78 | 13.69 |

The $^{13}C$ NMR and mass spectra are in agreement with the expected structure.

EXAMPLE 36

Preparation of 2-amino-4-methyl-6-anilinopyrimidine 3-oxide 20 g of 2-amino-4-methyl-6-chloropyrimidine 3-oxide, 25.65 g of aniline and 100 ml of ethanol are placed in a three-necked flask equipped with a condenser, a thermometer and a magnetic stirrer. The reaction medium is brought to 55° C. for 4 hours.

After the mixture has returned to room temperature, it is filtered through paper and then evaporated to dryness, and the oil is taken up in 10 ml of ethanol and then brought to pH 4 by adding ethanolic hydrogen chloride. 100 ml of ethyl ether are added. A beige product precipitates. This precipitate is filtered off, washed with ethyl ether, dried under vacuum and then taken up in 50 ml of sodium hydroxide. After 1 hour's stirring, the precipitate is filtered off, washed with water to neutrality and dried under vacuum over phosphorus pentoxide. It is recrystallized in 120 ml of dimethylformamide, and 3.1 g of 2-amino-4-methyl-6-anilinopyrimidine 3-oxide are obtained.

Yield=11.5%
Analyses:
M.p. 260° C.
Elemental analysis for $C_{11}H_{12}N_2O$; MW=216

|  | C | H | N | O |
| --- | --- | --- | --- | --- |
| Calculated | 61.12 | 5.50 | 25.92 | 7.40 |
| Found | 61.12 | 5.50 | 25.82 | 7.62 |

The $^1H$ NMR and mass spectra are in agreement with the expected structure.

EXAMPLE 37

Preparation of 2-amino-4-methyl-6-(N-methylphenethylamino)pyrimidine 3-oxide

The procedure described in Example 36 is followed, using N-methylphenethylamine.

Temperature=40° C.
Time : 3 hours
Recrystallization in acetonitrile
Yield=33%
M.p. 170° C.

Elemental analysis for $C_{14}H_{18}N_4O$; MW=258

|  | C | H | N | O |
| --- | --- | --- | --- | --- |
| Calculated | 65.12 | 6.98 | 21.70 | 6.20 |
| Found | 64.82 | 6.96 | 21.50 | 6.64 |

The $^1H$ NMR and mass spectra are in agreement with the expected structure.

EXAMPLE 38

Preparation of 2-amino-4-methyl-6-hexamethyleniminopyrimidine 3-oxide

The procedure described in Example 3 is followed, using hexamethylenimine.

Temperature=80° C.
Time : 3 hours
Recrystallization in acetonitrile/ethanol (70:30)
Yield=17%
M.p. 218° C.
Elemental analysis for $C_{11}H_{18}N_4O$; MW=222

|  | C | H | N | O |
| --- | --- | --- | --- | --- |
| Calculated | 59.46 | 8.10 | 25.22 | 7.20 |
| Found | 59.47 | 8.21 | 24.40 | 7.30 |

The $^1H$ NMR and mass spectra are in agreement with the expected structure.

EXAMPLE 39

Preparation of the internal salt of 2-amino-4,5-tetramethylene-6-butoxy-3-sulfooxypyrimidinium hydroxide 0.2 ml (0.003 mole) of chlorosulphonic acid is added with stirring to a solution, cooled in ice, of 1.2 ml (0.007 mole) of N,N-diisopropylethylamine in 6 ml of chloroform. After 30 minutes have elapsed, 0.237 g (0.001 mole) of 2-amino-4,5-tetramethylene-6-butoxypyrimidine 3-oxide is added and the mixture is maintained for 2 hours at between 0° and 5° C. under nitrogen. The solvent is evaporated off. The residue is taken up in a little water, and a white crystalline product is obtained and is filtered off. After recrystallization in a dimethylformamide/water mixture, 0.13 g of white crystals is obtained, the latter decomposing at 122° C.

Yield=41%
Elemental analysis for $C_{12}H_{19}N_3O_2S \cdot 0.21H_2O$; MW=317

|  | C | H | N | O | S |
| --- | --- | --- | --- | --- | --- |
| Calculated | 44.89 | 6.05 | 13.09 | 25.9 | 9.97 |
| Found | 44.89 | 6.08 | 13.09 | 26.02 | 9.93 |

The $^1H$ NMR and mass spectra are in agreement with the expected structure.

EXAMPLE 40

Preparation of the internal salt of 2-amino-4-methyl-6-(N-methylphenethylamino)sulphooxypyrimidinium hydroxide 1st method

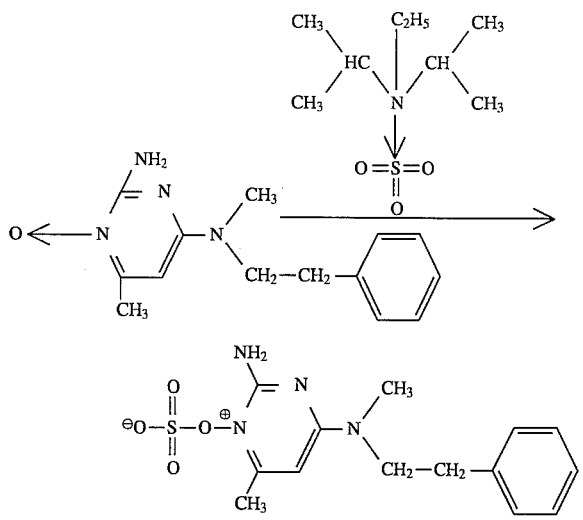

0.133 ml (0.002 mole) of chlorosulphonic acid is added with stirring to a solution, cooled in ice, of 0.72 ml (0.0042 mole) of N,N-diisopropylethylamine in 6 ml of chloroform. After 30 minutes have elapsed, 0.258 g (0.001 mole) of 2-amino-4-methyl-6-(N-methylphenethylamino)pyrimidine 3-oxide is added and the mixture is maintained for 3 hours at between 0° and 5° C. under nitrogen. The solvent is evaporated off. The residue is taken up in a little water, and a white crystalline product is obtained and is filtered off. After recrystallization in an acetonitrile/water mixture, 0.27 g of internal salt is obtained, the latter decomposing at 213° C.

Yield=80%

Elemental analysis for $C_{14}H_{18}N_4O_4S \cdot 0.25H_2O$; MW=338

|  | C | H | N | O | S |
|---|---|---|---|---|---|
| Calculated | 49.05 | 5.40 | 16.35 | 19.85 | 9.34 |
| Found | 48.98 | 5.29 | 16.27 | 19.94 | 9.43 |

The $^1H$ NMR and mass spectra are in agreement with the expected structure.

2nd method 0.32 g (0.002 mole) of sulphur trioxide/pyridine complex is added with stirring to a suspension of 0.258 g (0.001 mole) of 2-amino-4-methyl-6-(N-methylphenethylamino)pyrimidine 3-oxide in 3 ml of dimethylformamide. After 2 hours at 15°–20° C., 0.16 g (0.001 mole) of the complex is added and the mixture is left for a further hour at 15°–20° C. The solution obtained is diluted with 15 g of ice-cold water. The white precipitate obtained is filtered off and washed with ice-cold water. After recrystallization in an acetonitrile/water mixture, 0.24 g of internal sulphate is obtained, the latter decomposing at 213° C.

Yield=71%

EXAMPLE 41

Preparation of the internal salt of 2-amino-4-methyl-6-anilino-3-sulphooxypyrimidinium hydroxide The procedure of the first method described in Example 40 is followed, using 0.216 g of 2-amino-4-methyl-6-anilinopyrimidine 3-oxide. The products obtained, recrystallized in an acetonitrile/water mixture, decomposes above 260° C.

Yield=64%

Elemental analysis for $C_{11}H_{12}N_4O_4S$; MW=296

|  | C | H | N | O | S |
|---|---|---|---|---|---|
| Calculated | 44.59 | 4.05 | 18.92 | 21.62 | 10.82 |
| Found | 44.68 | 4.07 | 18.95 | 21.54 | 10.69 |

The $^1H$ NMR and mass spectra are in agreement with the expected structure.

EXAMPLE 42

Preparation of the internal salt of 2-amino-4-methyl-6-hexamethylenimino-3-sulphooxypyrimidinium hydroxide The procedure of the first method described in Example 40 is followed, using 0.222 g of 2-amino-4-methyl-6-hexamethyleniminepyrimidine 3-oxide. The product obtained, recrystallized in an acetonitrile/water mixture, decomposes above 195° C.

Yield=46%

Elemental analysis for $C_{11}H_{18}N_4O_4S$; MW=302

|  | C | H | N | O | S |
|---|---|---|---|---|---|
| Calculated | 43.71 | 5.96 | 18.54 | 21.19 | 10.60 |
| Found | 43.79 | 6.04 | 18.71 | 21.20 | 10.40 |

The $^1H$ NMR and mass spectra are in agreement with the expected structure.

FORMULATION EXAMPLES

A lotion intended for the treatment of hair loss having the following composition is prepared:

| Lotion 1 | |
|---|---|
| 2-Amino-4-methyl-6-piperidinopyrimidine 3-oxide (Example 1) | 5.0 g |
| Propylene glycol | 23.0 g |
| Ethanol | 55.0 g |
| Water | qs 100.0 g |
| Lotion 2 | |
| 2-Amino-4-methyl-6-piperidinopyrimidine 3-oxide (Example 1) | 2.0 g |
| Ethanol | 49.0 g |
| Water | qs 49.0 g |
| Lotion 3 | |
| 2-Amino-4-methyl-6-morpholinopyrimidine 3-oxide (Example 3) | 2.0 g |
| Propylene glycol | 4.9 g |
| Ethanol | 93.1 g |
| Lotion 4 | |
| 2-Amino-4-methyl-6-dimethylaminopyrimidine 3-oxide (Example 7) | 5.0 g |
| Propylene glycol | 23.0 g |
| Ethanol | 55.0 g |
| Water | qs 100.0 g |
| Lotion 5 | |
| 2-Amino-4-methyl-6-dimethylaminopyrimidine 3-oxide (Example 7) | 2.0 g |
| Propylene glycol | 4.9 g |
| Ethanol | 93.1 g |
| Lotion 6 | |
| 2-Amino-4-methyl-6-butyloxypyrimidine 3-oxide (Example 16) | 8.0 g |
| Propylene glycol | 23.0 g |

| | |
|---|---|
| Ethanol | 55.0 g |
| Water | qs 100.0 g |
| Lotion 7 | |
| 2-Amino-4-methyl-6-methoxypyrimidine 3-oxide (Example 14) | 1.0 g |
| Propylene glycol | 5.0 g |
| Ethanol | 94.0 g |
| Lotion 8 | |
| 2-Amino-4-methyl-6-ethoxypyrimidine 3-oxide (Example 15) | 5.0 g |
| Ethanol | 47.5 g |
| Water | 47.5 g |
| Lotion 9 | |
| 2-Amino-4-methylpyrimidine 3-oxide (Example 25) | 3.0 g |
| Ethanol | 30.0 g |
| Propylene glycol | 20.0 g |
| Water | qs 100.0 g |
| Lotion 10 | |
| 2-Amino-4-methylpyrimidine 3-oxide (Example 25) | 2.0 g |
| Propylene glycol | 4.9 g |
| Ethanol | 93.1 g |

1 to 2 g of each of these lotions is applied on the alopecic areas of the scalp, at the rate of one application per day for 7 days per week over 3 months.

We claim:

1. Compound of formula:

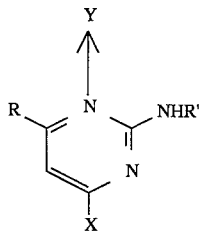

in which:

R is a hydrogen atom or a saturated linear $C_1$–$C_8$ alkyl radical or, with the pyrimidine ring, forms a carbon/hydrogen-containing ring, which is spiro on the carbon to which R is attached or is an ortho fusion placed with the adjacent carbon of the pyrimidine ring, of formula:

with n equal to 1, 2 or 3;

R' is a hydrogen atom or one of the following radicals:

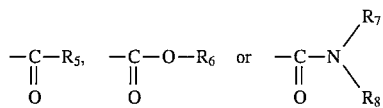

in which:

$R_5$ and $R_6$ are a $C_1$–$C_4$ lower alkyl radical; and $R_7$ and $R_8$ are a hydrogen atom or a $C_1$–$C_4$ lower alkyl radical, on condition that they do not simultaneously denote a hydrogen atom;

Y is an oxygen atom or an —$OSO_3^{\ominus}$ group; and

X is:

(i) a group $SR_4$, in which $R_4$ is a saturated linear or branched $C_1$–$C_{12}$ alkyl radical which can be substituted with a halogen atom or a trifluoromethyl radical, a linear $C_2$–$C_{12}$ alkenyl radical, a $C_3$–$C_{10}$ cycloalkyl radical, a $C_7$–$C_{12}$ aralkyl radical or a phenyl radical optionally substituted with one or two groups which, independently of one another, are a halogen atom, a $C_1$–$C_6$ alkyl radical, a $C_1$–$C_6$ alkoxy radical or a trifluoromethyl radical;

(ii) a group —$OR_3$ in which $R_3$ has the same meaning as $R_4$, on condition that, when Y is an oxygen atom, R an alkyl group and R' denotes a hydrogen atom, $R_3$ does not denote a $C_1$–$C_4$ alkyl radical or a phenyl group optionally substituted with one or two halogen atoms; as well as its cosmetically or pharmaceutically acceptable addition salts with acids.

2. Compound according to claim 1, selected from the group consisting of:

2 amino-4-methyl-6-(2,2-dimethylpropyloxy)pyrimidine 3-oxide;

2-amino-4-methyl-6-(1-cyclohexylmethyloxy)pyrimidine 3-oxide;

2-amino-4-methyl-6-(5-hexenyloxy)pyrimidine 3-oxide;

2-amino-4-methyl-6-benzyloxypyrimidine 3-oxide;

2-amino-4-methyl-6-(2,4-dimethylphenyloxy)pyrimidine 3-oxide;

2-amino-4-methyl-6-methylthiopyrimidine 3-oxide;

2-amino-4-methyl-6-ethylthiopyrimidine 3-oxide;

the inner salt of 2-amino-4-methyl-6-methoxy-3-sulphooxypyrimidinium hydroxide;

the inner salt of 2-amino-4-methyl-6-ethoxy-3-sulphooxypyrimidinium hydroxide;

2-amino-4,5-tetramethylene-6-butoxypyrimidine 3-oxide; and the inner salt of 2-amino-4,5-tetramethylene-6-butoxy-3-sulphooxypyrimidinium hydroxide.

* * * * *